United States Patent
Leuprecht

(10) Patent No.: US 7,750,200 B2
(45) Date of Patent: Jul. 6, 2010

(54) MATERIAL FOR PRODUCING A SUPPORT BANDAGE

(75) Inventor: Helmut Leuprecht, Vienna (AT)

(73) Assignee: Lohmann & Rauscher GmbH & Co. KG, Neuwied (DE)

( * ) Notice: Subject to any disclaimer, the term of this patent is extended or adjusted under 35 U.S.C. 154(b) by 263 days.

(21) Appl. No.: 11/721,654

(22) PCT Filed: Dec. 13, 2004

(86) PCT No.: PCT/EP2004/014181

§ 371 (c)(1), (2), (4) Date: Jun. 13, 2007

(87) PCT Pub. No.: WO2006/063599

PCT Pub. Date: Jun. 22, 2006

(65) Prior Publication Data

US 2009/0062712 A1    Mar. 5, 2009

(51) Int. Cl.
*A61F 13/00* (2006.01)

(52) U.S. Cl. .......................................... 602/41; 602/76

(58) Field of Classification Search ............. 602/41–59, 602/75–76
See application file for complete search history.

(56) References Cited

U.S. PATENT DOCUMENTS

| | | | | |
|---|---|---|---|---|
| 2,360,245 A | * | 10/1944 | McFarlane | .................. 442/47 |
| 2,523,865 A | * | 9/1950 | Dildilian | ...................... 428/62 |
| RE25,303 E | * | 12/1962 | Erikson | ........................ 51/297 |
| 3,973,670 A | * | 8/1976 | Spaar | .......................... 198/847 |
| 4,207,885 A | | 6/1980 | Hampton et al. | |
| 5,384,019 A | * | 1/1995 | Keating et al. | ............... 204/252 |
| RE39,176 E | * | 7/2006 | Dutt | ............................. 442/43 |

FOREIGN PATENT DOCUMENTS

| | | |
|---|---|---|
| DE | 20011824 U1 | 1/2002 |
| GB | 928099 | 6/1963 |
| JP | 33-4764 | 11/1931 |
| JP | 63-11165 | 1/1988 |
| JP | 64-014236 | 1/1989 |
| JP | 08-308919 | 11/1996 |
| JP | 09-099003 | 4/1997 |
| JP | 2000-199124 | 7/2000 |
| JP | 2000-343638 | 12/2000 |
| JP | 2001-353117 | 12/2001 |

OTHER PUBLICATIONS

Japanese Patent Application No. 2007-544744: Notification of Reasons for Rejection mailed Jan. 19, 2010.

* cited by examiner

*Primary Examiner*—Michael A. Brown
(74) *Attorney, Agent, or Firm*—Schwabe, Williamson & Wyatt, P.C.

(57) ABSTRACT

A material for producing a support bandage, which comprises a support. Said support is coated and/or impregnated with a curable plastic material and at least partially configured by a leno fabric comprising warp yarns that cross between two weft yarns running in parallel. Said leno fabric comprises at least one additional warp yarn that is located between two pairs of crossing warp yarns and does not cross any other warp yarn.

42 Claims, 1 Drawing Sheet

MATERIAL FOR PRODUCING A SUPPORT BANDAGE

CROSS REFERENCE TO RELATED APPLICATIONS

The present application is a national phase entry of, and claims priority under 35 U.S.C. §120 to, International Patent Application No. PCT/EP2004/014181, filed Dec. 13, 2004, entitled "Material for Producing a Support Bandage" and which designates the United States of America, the entire content and disclosure of which is hereby incorporated by reference in its entirety.

TECHNICAL FIELD

The invention pertains to a material to be used in the manufacture of a support bandage with a textile carrier that is coated and/or impregnated with a curable synthetic material and is formed at least in part with a leno fabric having two warp threads that cross one another between two parallel weft threads.

BACKGROUND

Materials with a textile carrier coated and/or impregnated with a curable synthetic substance are used as a replacement for plaster cast bandages, which offer poor wearing comfort on account of their great weight. These replacement materials can be produced in the form of rigid synthetic bandages by choosing appropriate synthetic materials and carriers with considerably less weight and the same amount of firmness or rigidity, while at the same time a sufficient degree of breathability is guaranteed. Such materials, moreover, can also be used to produce a bandage that remains slightly malleable even when cured if curable synthetic materials with the appropriate properties are used.

Conventional synthetic rigid bandages are available in form of a linear, bandage-like material and are wrapped around the body part requiring support to form the support bandage, with hardening of the synthetic material being effected using appropriate procedures before, during, and/or after application of the bandage. Depending on the synthetic material, hardening can be effected through ultraviolet treatment, heat curing, or hardening with the aid of a solvent. Hardening with the aid of cold water as the solvent has proved to be especially useful because it avoids dermal reactions as for instance irritation of the skin caused by warming of the synthetic material.

To fit the conventional material to the part of the body in question, textile carriers can be used that are extensible either lengthwise or widthwise, with the shaping of the carrier effected during application of the bandage being fixed as the synthetic material is hardened. To retain the desired flexibility, in the case of conventional synthetic rigid bandages, knitted glass fiber carriers are used that derive their flexibility in the transverse direction, i.e. in the fill direction of the carrier, from the mesh structure of the knitted material, and the malleability of which in the longitudinal direction of the linear, bandage-type material, i.e. in the warp direction of the woven carrier, is attributable to the rigidity of the glass fiber, so that the individual meshes of the woven carrier remain malleable in the warp direction as well.

Materials produced using textile carriers of the kind specified above are described, for instance, in U.S. Pat. No. 3,787,272.

Use of these materials is problematic, however, in that when such support bandages are cut, glass fiber dust may be generated that is suspected of being injurious to health.

In view of these problems, manufacture of textile carriers from other synthetic fibers, e.g. polyester yarn and polyamide yarn, has already been proposed. These yarns exhibit a rigidity that is considerably less than that of glass fibers, however, so that when such yarns are used, materials produced for the manufacture of support bandages usually exhibit a sufficient extensibility in the transverse direction, i.e. in the fill direction of the woven textile carrier, while they retain only a very minor malleability in the longitudinal or warp direction. For that reason, materials produced using such carriers adapt themselves poorly to body shape. As a solution to this problem, a woven carrier is being proposed, in European Patent No. EP 0 356 446 B1, for a material for the manufacture of a support bandage in which the longitudinal warp threads are made of a heat-shrinkable material. The carrier described in this publication is initially woven with yarn that is generally available as multiple filament yarn, then subjected to a heat treatment. The heat treatment results in a shrinking in the warp threads that run in the longitudinal direction of the carrier, which gives these warp threads, and the carrier as a whole, a change of structure which in turn makes possible an extension of the warp threads and, consequently, of the entire carrier in the longitudinal direction.

Although a satisfactory adaptation of the bandage material to the shape of the body can be achieved using such carriers, production of these carriers is problematic.

In view of these problems in the state of the art, it has been proposed, in German Patent Application No. DE 200 11 824, to introduce a support bandage carrier of the kind described above. By using a leno fabric, which is simple to produce in comparison with knitted structures, the problems of production cited above to can be solved, while at the same time achieving satisfactory form stability of the carrier material. In the process, production of the known materials with a carrier in the form of a leno fabric is simplified as a result of the fact that one of the intersecting warp threads runs under the weft thread and the other of the intersecting warp threads runs over the weft threads, whereby the warp thread that runs beneath the weft threads is located at the points of intersection above the warp thread that runs over the weft thread.

Although such materials are easily produced and guarantee stability of form, and although the extensibility that is desired for conformability to body shape can thereby be ensured, it has been shown that the long-term stability of these materials leaves something to be desired.

BRIEF DESCRIPTION OF THE DRAWINGS

Embodiments of the present invention will be readily understood by the following detailed description in conjunction with the accompanying drawings. To facilitate this description, like reference numerals designate like structural elements. Embodiments of the invention are illustrated by way of example and not by way of limitation in the FIGURE of the accompanying drawings.

DETAILED DESCRIPTION OF EMBODIMENTS OF THE INVENTION

Figure 1:
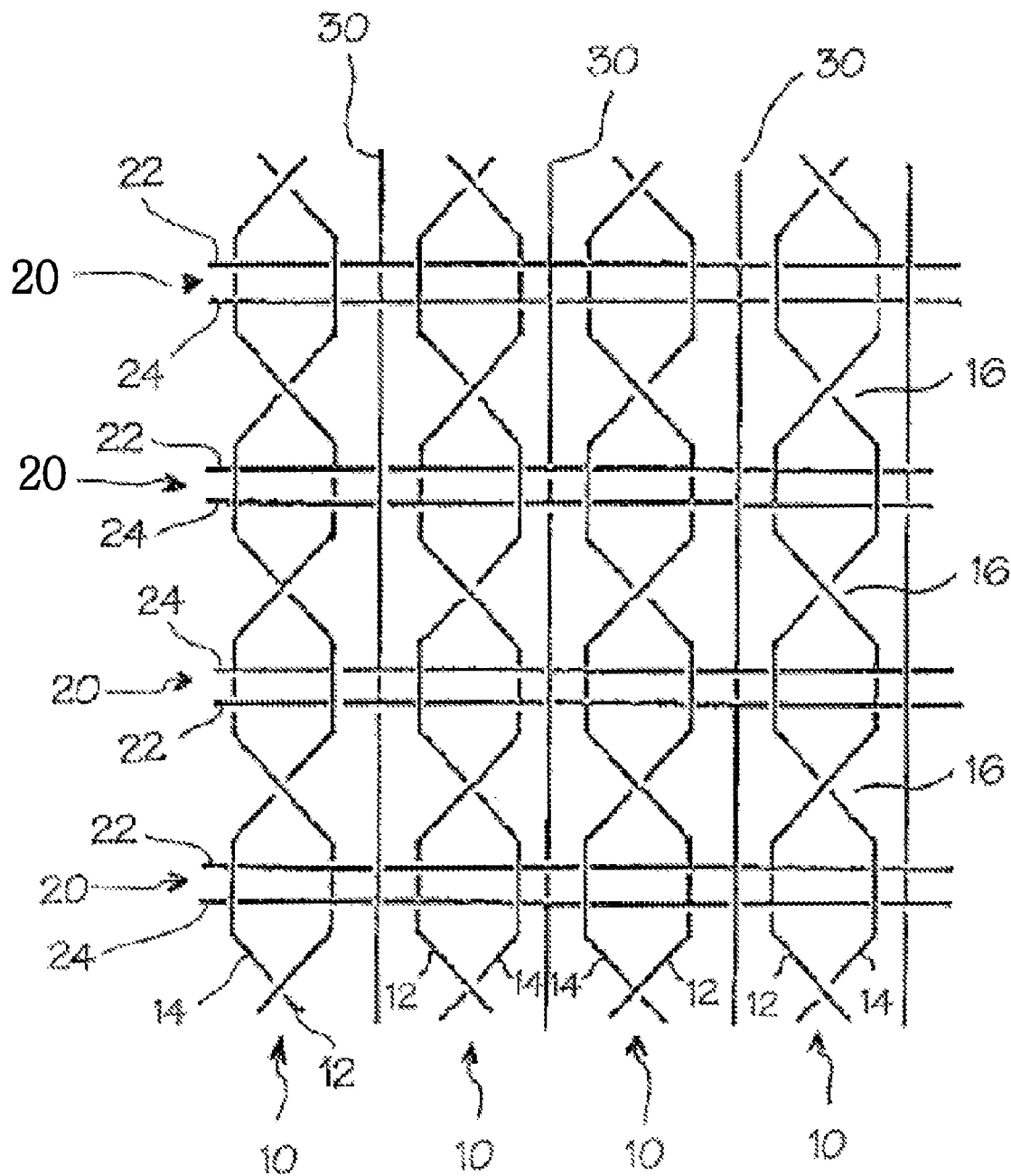
FIG. 1 is a schematic representation of an exemplary carrier in accordance with various embodiments.

In view of these problems in the state of the art, the task that underlies this invention is to describe a further elaboration of available materials that remains stable even with prolonged use.

According to the invention, this task is accomplished through a further elaboration of the known material, characterized essentially in that the leno fabric has at least one additional warp thread that is located between two pairs of intersecting warp threads and that does not cross any other warp thread.

This invention is based on recognition of the fact that although an especially good stability of form is achievable, in comparison with traditional fabrics, through the good anchorage of the weft threads by means of the intersecting warp threads of a leno fabric, the structural integrity of the material, in the direction of its thickness, i.e., perpendicular to the surface defined by the warp and the weft threads, is unsatisfactory because the individual warp threads of a conventional leno fabric always run on only one side of the weft threads. This leads to inadequate adhesion of the synthetic material that has been applied to the carrier; further, it can also cause individual warp threads to slip out at the edges of the material. These effects cause the problems that have been observed and described above with regard to the long-term stability of conventional materials. Through use of additional warp threads, the materials that have been further elaborated according to our invention counteract these effects; on the one hand, they produce structural integrity of the material in the direction of its thickness, on the other hand they guarantee a good anchorage of not only the weft threads but the warp threads of the material as well.

With regard to the technical aspect of production, it has proven to be especially advantageous if at least one additional warp thread exhibits at least one second segment running on one side of the weft threads that is turned away from a first segment of the warp thread, whereby the changeover from the first segment to the second segment occurs preferably between those parallel weft threads between which the warp threads of at least one pair of intersecting warp threads cross one another as well. Here the structural integrity of the material can be further increased in the direction of its thickness if of two additional warp threads, located on opposite sides of a pair of intersecting warp threads, one additional warp thread is located in the area of the weft threads on the side of the weft threads that is turned away from the other additional warp thread. In order to prevent slipping out of individual warp threads at the edge of the material, which can cause fraying of the material on this edge, it has proved to be especially advantageous if at least one additional warp thread and/or at least one weft thread is texturized.

As can be seen from the above description of known materials, in the case of the material according to the invention, at least one warp thread of a pair of intersecting warp threads and/or at least one additional warp thread and/or at least one weft thread is preferred to be extensible, preferably elastically extensible, and it is especially advantageous if it consists of an elastically extensible material, as for example elastic polyurethane. The warp thread that consists at least partially of elastic material may have a core filament of elastic yarn, as for example polyurethane yarn, preferably wrapped around twice by yet another yarn, as for example a polyester yarn.

With the use of conventional materials of the kind described above, constriction due to tensile loading and/or formation of bulge-like creases can sometimes be observed. In the case of a rigid bandage for the lower leg, such bulge-like creases may develop in the shape of a ring around the ankle and on the forefoot, running parallel to the warp direction of the carrier material.

According to a further aspect of the invention, it is proposed with regard to these problems that for a material having a carrier in the form of a leno fabric, at least one weft thread of the leno fabric consist, at least in segments, of a high-strength yarn, as for example a polyester yarn.

This solution to the problem rests on the knowledge that formation of such constrictions and bulge-like creases is caused by insufficient transverse stability in the conventional material used in the carrier. This insufficiency can be remedied, in accordance with the aspect of the invention just described, through use of a high-strength weft thread, because this high-strength weft thread, as for example in the form of a polyester yarn, lends increased transverse rigidity to the carrier material.

To preserve the desired extensibility, heat-shrinkable warp threads and/or weft threads can be used that can be subjected either before or after the weaving process to a heat treatment in order to maintain a flexible structure. Alternatively, or in addition, the fabric of the material according to this invention can also have either warp threads or weft threads made of an elastomer material that derive their extensibility from the characteristics of the material itself and not from the structure of the yarn.

With regard to an adequate stability of the material while securing a satisfactory conformability to the body shape, it has proved to be especially advantageous if the material, in the direction of the warp threads of the fabric, exhibits an extensibility of at least 20%, with a preferred extensibility of at least 30%, especially preferred from 60 to 95%, prior to hardening of the synthetic material, whereby the material in the direction of the warp threads of the fabric, in unextended condition, advantageously exhibits a tensile strength of at least 10 N/cm, preferably at least 20 N/cm, and especially preferred between 30 and 60 N/cm.

From the same vantage points (conformability to the body shape and stability of the material), it has proved to be advantageous if, prior to hardening of the synthetic material, the material has an extensibility of at least 30%, preferably at least 40%, and especially preferred from about 50 to 100%, whereby the tensile strength of the material in the direction of the weft threads of the fabric in unextended condition advantageously amounts to 10 N/cm, preferably to at least 20 N/cm, especially preferred to about 30 to 50 N/cm.

A relatively low weight of the materials according to this invention can be maintained, while at the same time a sufficiently high degree of stability can be safeguarded, if the fabric, in unextended condition, has a weight per unit area of approximately 50 to 250 $g/m^2$, preferably from approximately 100 to 200 $g/m^2$.

The weft and/or warp threads of the fabric of the material according to the invention may, for example, comprise natural fibers. But especially good characteristics can be obtained if the weft and/or warp threads of the fabric comprise synthetic fibers, either additionally or alternatively, as for example polyamide fibers, polyester fibers, polypropylene fibers, or similar fibers, because such synthetic fibers make possible an especially good calibration of extensibility, tensile strength, and other mechanical characteristics. In addition, the weft and/or warp threads can be texturized, at least in part, to ensure extensibility. This texturization can be obtained by heat treatment of the fibers or by treatment of the fibers with a solvent.

As is the case with the known materials according to German Patent Application No. DE 200 11 824, the leno fabrics of materials according to this invention can be produced in an especially simple way and while safeguarding an especially high degree of stability, if one of the intersecting warp threads in at least one pair of intersecting warp threads runs underneath the weft threads, the other of the intersecting warp threads runs on top of the weft threads, and the warp thread that runs underneath the weft threads is located at the intersection point above the warp thread that runs on top of the weft threads. Further, an especially high degree of stability of such carriers in the form of a leno fabric can be obtained if at least two weft threads are located between successive intersection points of the warp threads and/or successive changeover points of at least one additional warp thread. It has proved especially advantageous, with regard to obtaining the desired increased transverse rigidity while safeguarding the equally desired structural integrity, if at least one of the weft threads placed between successive intersections and/or successive crossovers is texturized and another of these weft threads is formed out of high-strength and preferably smooth yarn, in particular polyester yarn. With the high-strength yarn, the desired transverse rigidity is ensured, while with the texturized weft thread the desired structural integrity is improved.

In this description, every thread segment that runs essentially in a straight line and perpendicular to the warp threads is being called "weft thread." For achieving an especially good stability of the carrier fabric of the material according to this invention, it has proved advantageous if the individual weft threads are in the form of thread segments, of which at least two are linked together over a connecting segment located at the edge of the fabric, whereby this connecting segment may be of a piece with the thread segments that form the weft thread. The occurrence of tears or other kinds of damage at the edge of the fabric can be avoided if at least one linking segment that connects two weft threads with one another wraps around at least one, preferably at least two, preceding weft threads so as to form in this manner a fabric edge out of linked fiber segments.

With regard to achieving as high a degree of stability and extensibility as possible of a material according to this invention and at the same time safeguarding the lowest possible weight, it has proved to be advantageous if the fabric in its unextended state exhibits from approximately 40 to 80, preferably approximately 66 warp threads, i.e. approximately 20 to 40 if a leno fabric is used, preferably approximately 33 double threads in the warp direction and/or approximately 80 to 150, preferably approximately 132 weft threads, i.e. 40 to 75, preferably approximately 66 double weft threads, if the leno fabric described above is used, for 10 cm of fabric length and/or width.

As already explained above, the hardenable synthetic material may comprise a thermosetting or UV-hardenable synthetic material. To be sure, the manufacture of a material according to the invention will preferably involve the use of a synthetic material curable with a solvent, in particular cold water. With regard to obtaining a maximum degree of skin compatibility and at the same time safeguarding the desired mechanical characteristics, use of a synthetic material that comprises a moisture-curing polyurethane prepolymer has proved to be especially advantageous. Synthetic materials of this kind are described in European Patent No. EP 0 093 780 B1, for example, the disclosure content of which with regard to the curable synthetic materials described therein is hereby incorporated into this description by direct reference. The synthetic material according to the invention may suitably comprise approximately 30 to 70% of the weight of the material according to the invention.

As can already be surmised from the preceding description of the material according to this invention, the carrier used for producing this material, according to the invention, is characterized essentially in that it exhibits a woven structure, with the carrier realized in the form of a leno fabric with additional warp threads that do not cross any other warp threads. With the aid of such a carrier, the material according to this invention can be produced by a process according to the invention in which the carrier is coated and/or impregnated with a curable synthetic material, with the carrier being subjected to heat treatment, either before or after coating and/or impregnation with the synthetic material, in order to thus endow the material in total with the desired extensibility.

Below, the invention is described with reference to FIG. 1, to which the reader is expressly referred with regard to all essential details regarding the invention not set forth more prominently in the description. FIG. 1 shows a schematic representation of the embodiment of a carrier according to this invention to be used in the manufacture of a material according to the invention.

FIG. 1 shows a section of a carrier according to the invention for a material for the manufacture of a support bandage in the form of a leno fabric with four warp thread pairs (10), with intersecting warp threads (12 and 14), a total of four weft thread pairs (20) and three additional warp threads (30). Each of the warp thread pairs (10) comprises a warp thread (12) that runs underneath the pair of weft threads (20) as well as one warp thread (14) that runs on top of the pair of weft threads (20). Warp thread (12), which runs underneath the pair of weft threads (20), crosses warp thread (14), which runs on top of the pair of weft threads (20), of the pair of warp threads (10) at crossover points (16). At these crossover points (16), warp thread (12), which runs beneath the pair of weft threads (20), is placed on top of warp thread (14), which runs on top of the pair of weft threads (20). Between each two successive crossover points (16) of the pair of warp threads (10), a pair of weft threads (20) are located, with the crossover points of the individual pairs of warp threads (10) lying approximately on a straight line that runs parallel to the pairs of weft threads (20). Using the structure of a leno fabric as shown in FIG. 1, the pairs of weft threads (20) are firmly secured, thus preventing slippage of individual threads during coating or impregnation with the curable synthetic material, as for example with a polyurethane prepolymer.

Each of the pairs of weft threads (20) contains a smooth weft thread (22) of a high-strength polyester yarn and a texturized weft thread (24), which is also made of a polyester yarn.

Additional warp threads (30) that do not cross any other warp threads are located between the pairs of warp threads (10); individual segments of these additional warp threads run on top of the weft threads and other segments run beneath the weft threads. The changeover between the segments that run on top of the weft threads and those segments that run beneath the weft threads occurs between those weft threads between which the warp threads (12 and 14) of the pair of warp threads (10) also cross one another. FIG. 1 shows that of two additional warp threads (30) located on opposite sides of the pair of intersecting warp threads (12 and 14), an additional warp thread (30) is located in the area of the weft threads on the side of these weft threads (22, 24) that is turned away from the other additional warp thread 30.

The invention is not limited to use of the leno fabric that is described by means of FIG. 1. In fact, yarns comprised of natural fibers, polyamide fibers, polypropylene fibers and other similar fibers can be used for the manufacture of a carrier according to this invention. The extensibility of the carrier produced using polyamide fibers may amount to 80 to 90% in the warp direction in the prepared state, i.e. when treated with the synthetic material and unextended. This means that the unextended fabric may be extended in the warp direction from 100 to 180-190%. In the weft direction, extensibility of a carrier made of polyamide fibers may amount to 120-130% in the treated (unextended) state. This means that this fabric can be stretched from 100 to 220 or as much as 230%. In an extended state, the coating weight per unit area can thereby amount to from 50 to 55 g/m². When polyamide fibers are used for the manufacture of the warp- and weft threads, a warp thread size ranging from 40 to 60 tex may be used, preferably about 46.8 tex, as well as a weft thread size ranging from 20 to 40, preferably about 31.2 tex.

Further, new synthetic materials can also be used within the context of this invention, in particular synthetic materials in the form of a moisture-curable polyurethane prepolymer suited for use with polyamide.

The invention claimed is:

1. A material for producing a support bandage, comprising:
   a carrier at least partially in the form of a leno fabric and coated and/or impregnated with a curable synthetic material, the carrier including at least two pairs of intersecting warp threads, each pair intersecting between at least two pairs of parallel weft threads, the carrier further including at least one additional warp thread located between two pairs of the at least two pairs of intersecting warp threads and crossing no other warp thread.

2. The material of claim 1, wherein the at least one additional warp thread includes at least one second segment that runs on a side of a pair of the weft threads that is turned away from a first segment of the at least one additional warp thread, whereby a changeover between the first segment and the second segment occurs between the at least two pairs of parallel weft threads between which the warp threads of at least one pair of the intersecting warp threads also intersect.

3. The material of claim 1, wherein the at least one additional warp thread comprises two additional warp threads located on opposite sides of a pair of intersecting warp threads, and wherein one of the two additional warp threads is located in an area of the weft threads on a side of the weft threads that is turned away from the other one of the two additional warp threads.

4. The material of claim 1, wherein the at least one additional warp thread is texturized.

5. The material of claim 1, wherein a selected one or more of at least one warp thread of a pair of intersecting warp threads, the at least one additional warp thread, and at least one weft thread is extensible.

6. The material of claim 5, wherein the selected one or more comprises elastic polyurethane.

7. The material of claim 5, wherein the at least one warp thread comprises an elastic material and includes a filament core comprising an elastic yarn.

8. The material of claim 7, wherein the elastic yarn comprises a polyurethane yarn.

9. The material of claim 7, further comprising another yarn wrapped around the filament core.

10. The material of claim 9, wherein the other yarn is a polyester yarn.

11. The material of claim 1, wherein the carrier is coated and/or impregnated with a hardenable synthetic material, and wherein at least one of the weft threads comprise a high-strength yarn.

12. The material of claim 11, wherein the high-strength yarn comprises a polyester yarn.

13. The material of claim 1, wherein the leno fabric includes heat-shrinkable warp threads and/or weft threads.

14. The material of claim 1, wherein the warp threads and/or the weft threads comprise an elastomer material.

15. The material of claim 1, wherein the material, in the direction of the warp threads, has an extensibility of at least 20%.

16. The material of claim 15, wherein the extensibility is between about 65 and about 95%.

17. The material of claim 1, wherein the material, in the direction of the warp threads and in an unextended state, has a tensile strength of at least 10 N/cm.

18. The material of claim 17, wherein the tensile strength is between about 30 and about 60 N/cm.

19. The material of claim 1, wherein the material, in the direction of the weft threads and prior to hardening of the synthetic material, has an extensibility of at least 30%.

20. The material of claim 19, wherein the extensibility is between about 50 and about 100%.

21. The material of claim 1, wherein the material, in the direction of the weft threads and in an unextended state, has a tensile strength of at least 10 N/cm.

22. The material of claim 21, wherein the tensile strength is between about 30 and about 50 N/cm.

23. The material of claim 1, wherein the material, in an unextended state, has a weight per unit area of between about 50 and about 250 g/cm².

24. The material of claim 23, wherein the weight per unit area is between about 100 and about 200 g/m².

25. The material of claim 1, wherein the weft and/or the warp threads comprise natural fibers.

26. The material of claim 1, wherein the weft and/or the warp threads comprise synthetic fibers.

27. The material of claim 26, wherein the weft and/or the warp threads comprise one or more of polyamide fibers, polyester fibers, and polypropylene fibers.

28. The material of claim 1, wherein the weft and/or the warp threads are at least partially texturized to maintain extensibility.

29. The material of claim 1, wherein at least one pair of the intersecting warp threads includes one warp thread running underneath the weft threads, and the other warp thread running on top of the weft threads, and wherein the warp thread running underneath the weft threads is located at points of intersection above the warp thread running above the weft threads.

30. The material of claim 1, wherein at least a pair of the weft threads is located between successive points of intersection of the warp threads and/or successive changeover points of the at least one additional warp thread.

31. The material of claim 30, wherein one of the weft threads of the pair of the weft threads is texturized and the other weft thread of the pair of the weft threads comprises a high-tensile yarn.

32. The material of claim 31, wherein the high-tensile yarn comprises a polyester yarn.

33. The material of claim 1, wherein the weft threads comprise thread segments, and wherein at least two of the thread segments are linked with one another over at least one connecting segment located at an edge of the leno fabric.

34. The material of claim 33, wherein the at least one connecting segment wraps around at least one preceding weft thread.

35. The material of claim 1, wherein the leno fabric, in an unextended state, comprises between about 40 and about 80 warp threads per 10 cm of the leno fabric length and/or width, and between about 80 and about 150 weft threads per 10 cm of the leno fabric length and/or width.

36. The material of claim 35, wherein the leno fabric, in an unextended state, comprises about 66 warp threads per 10 cm of fabric length and/or width and/or about 132 weft threads per 10 cm of fabric length and/or width.

37. The material of claim 1, wherein the synthetic material is curable with a solvent.

38. The material of claim 37, wherein the synthetic material is curable with water.

39. The material of claim 37, wherein the synthetic material comprises a moisture-hardening polyurethane prepolymer.

40. The material of claim 1, comprising between about 30 and about 70% of the synthetic material by weight.

41. A carrier for a material comprising:
   at least two pairs of intersecting warp threads;
   at least two pairs of parallel weft threads; and
   at least one additional warp thread located between two pairs of the at least two pairs of intersecting warp threads and crossing no other warp thread;
   wherein each pair of intersecting warp threads intersect between at least two pairs of the parallel weft threads.

42. A method for making a material for producing a support bandage, comprising:
   providing a carrier including:
      at least two pairs of intersecting warp threads;
      at least two pairs of parallel weft threads; and
      at least one additional warp thread located between two pairs of the at least two pairs of intersecting warp threads and crossing no other warp thread;
      wherein each pair of intersecting warp threads intersect between at least two pairs of the parallel weft threads; and
   coating and/or impregnating the carrier with a curable synthetic material.

* * * * *